United States Patent [19]

Sommer

[11] Patent Number: Plant 5,347

[45] Date of Patent: Nov. 20, 1984

[54] KALANCHOE PLANT

[75] Inventor: Heinz Sommer, Zuchwil, Switzerland

[73] Assignee: Mikkelsens, Inc., Ashtabula, Ohio

[21] Appl. No.: 439,645

[22] Filed: Nov. 5, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct Kalanchoe hybrid named Mercur characterized by its deep orange flower color, highly floriferous habit, sturdy, upright self-branching plant form with above average keeping qualities, and its adaptability to 10–15 cm. pot plant production on year around basis in controlled environments.

1 Drawing Figure

The present invention relates to a new and distinctive variety of kalanchoe plant, botanically known as kalanchoe, and referred to by the cultivar name Mercur. Mercur was developed by me through controlled breeding in Zuchwil, Switzerland by crossing Regulus (U.S. Plant Pat. No. 4,817) as the seed parent with Mars (unpatented) as the pollen parent. Asexual reproduction of stem cuttings taken in Zuchwil, Switzerland has shown that the unique features of Mercur are stabilized and are reproduced true to type in successive propagations.

The following characteristics distinguish the new kalanchoe from both its parent varieties and other cultivated kalanchoes of this type known and used in the floriculture industry:

1. In comparison to Regulus, my new cultivar flowers 7–10 days earlier, has a more pleasing orange color in the flowers, less crenation on the leaf margin, and has much better root growth.

2. The cultivar Feuerball flowers 14–18 days later than Mercur, has orange/red flowers, considerable splitting of the calyx, is slower growing, and its flowers are very susceptible to botrytis and mildew.

3. In comparison to Rotkappchen, disclosed in U.S. Plant Pat. No. 3,851, Mercur has darker orange flowers, more compact growth, smaller foliage, and a more pleasing plant form.

4. In comparison to Nugget, disclosed in U.S. Plant Pat. No. 4,207, Mercur has deeper orange flowers, more uniform and 7–10 days later flowering, and has larger, darker foliage with crenated margins.

5. In comparison to Sirius, disclosed in U.S. Plant Pat. No. 4,103, the flower color of Mercur is somewhat deeper orange, the foliage is more uniform in size so that plant and flower presentation is more proportional, and the flowering is slower.

6. Generally, Mercur has better overall qualities of growth, plant and flower keeping quality, and is more resistent to botrytis, flower blight and mildew infection on the foliage than the before mentioned cultivars.

7. Additionally, Mercur has a high degree of self-branching. This is valuable for cutting production and producing of full flowering plants in 10–15 cm. pots.

8. Mercur responds well to the growth regulators Cycocel and A-Rest. However, Mercur does not tend to have long internodal growth so that regulators are only needed under extremely adverse environments.

9. Flowers on Mercur tend to be night closing until the reproductive parts are well developed. This is a quite different character than found in Regulus.

10. In comparison to Cinnabar, disclosed in the U.S. plant patent application of James C. Mikkelsen, filed Sep. 15, 1982, Mercur is deep orange in flower color, whereas Cinnabar is an orange/red to light red. Cinnabar is much more vigorous, needing more growth regulation in comparison to Mercur.

The accompanying colored photograph taken in February 1982 illustrates in perspective view the overall appearance of Mercur grown in a 10 cm. plastic pot, and showing the colors as true as it is reasonably possible to obtain in a colored reproduction of this type.

The following is a detailed description of my new kalanchoe variety based on plants produced under commercial practices in greenhouses of Wyss Samen und Pflanzen A.G., Zuchwil, Switzerland, and Mikkelsens, Inc., Ashtabula, Ohio. Color references are made to The Royal Horticultural Society Colour Chart except where general terms of ordinary dictionary significance are used.

PARENTAGE

A controlled cross of the cultivar Regulus as the seed parent and the cultivar Mars as the pollen parent.

PROPAGATION

Type cutting: Stem or tip cuttings 2 cm. long.

Time to root: 10–12 Days at 21° C. summer; 14–16 days at 21° C. winter.

Rooting habit: Abundant, fibrous, dendritic.

PLANT DESCRIPTION

Form: Upright, closely internoded, self-branching, compact, succulent.

Habit of growth: Average rate of upright growth, with self-branching at nearly every node.

Foliage: Leaves are simple, opposite, symmetrical.

(1) *Size.*—Mature foliage 6–7 cm. wide and 10–12 cm. long.

(2) *Shape.*—Elliptical, apex and base obtuse.

(3) *Texture.*—Glabrous, coriaceous, succulent.

(4) *Margin.*—Broadly crenated.

(5) *Color.*—Young foliage top side, green 147B; under side, green 148A. Mature foliage top side, between green 147A and 147B; underside, green 147B.

FLOWERING DESCRIPTION

Flowering habit: Inflorescence of each peduncle is formed by dichotomous branching, with the terminal flower on the main axis flowering first followed by the terminal flowers on the side branches of the inflorescence. Individual flowers remain in bloom 2-3 weeks, and total flowering covers a period of 2 or more months.

Natural flowering season: Early to mid-January at 50° north latitude. Flowering time under controlled day length at 18°-19° C. night temperature in summer is 9-10 weeks; in winter 12-13 weeks. Flowering time is variable depending on the amount of light energy available.

Flower buds: Before opening buds are generally oblong up to 6-7 mm. long, then becoming tubular as flower petals develop, sheathed with four green sepals. Corolla at maturity 10-11 mm. long.

Flowers borne: On pedicels 5-6 mm. long from the compound dichasial cyme with strong peduncles. Both the pedicel and peduncle lengths can be controlled with growth regulators.

Quantity of flowers: Very floriferous with 50-75 buds per major axillary peduncle in flower, and secondary buds that follow.

Petals:

(1) *Shape.*—Nearly oval, apex cuspidate.

(2) *Color.*—Top side when opening, orange red 33A, slight fading to orange red 34C; underside, orange red 33C.

(3) *Number of petals.*—Four, united in corolla, salvaform; petals 6-7 mm. in diameter, total flower diameter up to 15 mm.

Reproductive organs:

(1) *Stamens.*—8 In number. (a) Anther shape: flat, elliptical, color light yellow. (b) Filament color: light, translucent green (c) Pollen color: yellow.

(2) *Pistels.*—(a) Stigma shape: flat, crystalline, white in color with green tinge. (b) Style color: light green. (c) Ovaries: 4 in number; celled, size 4-5 mm; color green.

DISEASE RESISTANCE

In the test areas, when grown with a broad spectrum of kalanchoe cultivars, this cultivar shows high resistance to botrytis, flower blight and powdery mildew.

I claim:

1. A new and distinct cultivar of Kalanchoe plant known by the cultivar name Mercur, as described and illustrated, and particularly characterized by its deep orange flower color, highly floriferous habit, sturdy, upright self-branching plant form; above average keeping qualities; relatively dark green foliage with crenated margins, and by its adaptability to 10-15 cm. pot production on a year round basis in controlled environments.

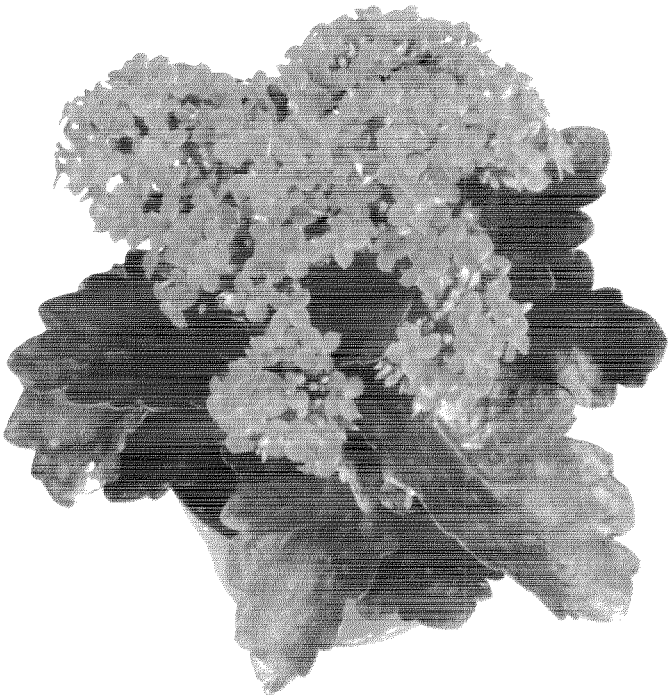

* * * * *